`US005239077A`

United States Patent [19]

Bertok et al.

[11] Patent Number: 5,239,077
[45] Date of Patent: Aug. 24, 1993

[54] HIGHLY PURE AMIDOXIMES

[75] Inventors: Bela Bertok, Budapest; Istvan Szekely, Dunakeszi; Angelika Thurna, Budapest; Lajos Nagy, Szentendre; Eva Somfai, Budapest; Sandor Botar, Budapest; Antal Gajary, Budapest; Kalman Takacs, Budapest, all of Hungary

[73] Assignee: Chinoin Gyogyszar es Vegyeszeti Termekek Gyara Rt., Budapest, Hungary

[21] Appl. No.: 602,287
[22] PCT Filed: Jan. 10, 1990
[86] PCT No.: PCT/HU90/00003
    § 371 Date: Nov. 9, 1990
    § 102(e) Date: Nov. 9, 1990
[87] PCT Pub. No.: WO90/08131
    PCT Pub. Date: Jul. 26, 1990

[30] Foreign Application Priority Data

Jan. 10, 1989 [HU] Hungary .................. 70/89

[51] Int. Cl.$^5$ ............................ C07D 401/12
[52] U.S. Cl. .................................... 546/193
[58] Field of Search .................. 546/193; 514/318

[56] References Cited

U.S. PATENT DOCUMENTS 4,187,220 2/1980 Takacs ..................... 546/23

FOREIGN PATENT DOCUMENTS 0121701 10/1984 European Pat. Off. .
2927117  1/1984 Fed. Rep. of Germany .
3620166A1 12/1987 Fed. Rep. of Germany .
 634828  2/1983 Switzerland .
1582029 12/1980 United Kingdom .

OTHER PUBLICATIONS

Appl. Polym. Sci. 11, pp. 145–148 (1967).
Monatshefte fur Chemie, 154, pp. 118 to 131 (1894).
Houben Weyl, vol. X/4, pp. 217–220 (1968).
J. Am. Chem. Soc., vol. 80, pp. 1257–1259 (1958).
J. Chem.Soc. 1950, pp. 2257 to 2272.
J. Org. Chem. 33, (2) pp. 523–530 (1968).

Primary Examiner—C. Warren Ivy
Assistant Examiner—Celia Chay
Attorney, Agent, or Firm—Herbert Dubno

[57] ABSTRACT

The inventions is a purer form of O-(2-hydroxy-3-piperidino-1-propyl)nicotinic acid amidoxime hydrochloride.

1 Claim, No Drawings

HIGHLY PURE AMIDOXIMES

FIELD OF THE INVENTION

This invention relates to an improved process for preparing amidoxime derivatives.

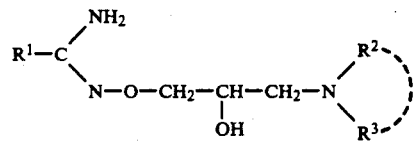

In the formulae used herein, the meaning of the substituents is throughout as follows if not indicated otherwise:

$R^1$ means a $C_{2-15}$ group, which may be unsaturated and/or cyclic alkyl, aralkyl group or optionally substituted and/or condensed aromatic and/or heteroaromatic group;

$R^2$ stands for hydrogen or an optionally substituted straight or branched chain or cyclic and/or unsaturated $C_{1-7}$ alkyl or aromatic group;

$R^3$ represents an optionally substituted straight or branched chain or cyclic and/or unsaturated $C_{1-7}$ alkyl or aromatic group; or $R^2$ and $R^3$ together with the adjacent nitrogen atom may form an 5- to 8-membered ring optionally containing other heteroatoms; and X stands for halogen.

BACKGROUND OF THE INVENTION

It is known that several representatives of amidoxime derivatives of the formula (I)

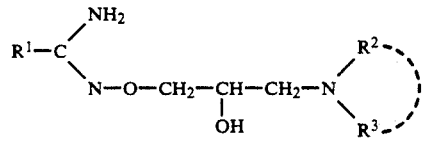

are useful for the treatment of diabetic angiopathy which is practically unique to the present. Other amidoxime derivatives show a blood pressure lowering action, too and, an alpha-blocking effect may also be observed (British patent specification No. 1,582,029; U.S. Pat. Nos. 4,187,220 and 4,308,399). The possibility of the use of these compounds as therapeutic drugs demands an economical preparation which can be carried out on an industrial scale.

It is known that O-substituted derivatives of oximes are usually prepared by employing alkylating agents (Houben Weyl Vol. X/4, pages 217 to 220 (1968). The O-substituted amidoximes according to the present invention have been prepared by reacting amidoximes with epoxides (or their functional equivalents), i.e. with the epoxy compounds of the formula (IV)

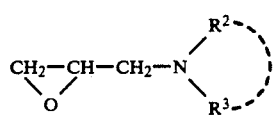

or with 1-halo-2-hydroxy-3-propanamines of the formula (III)

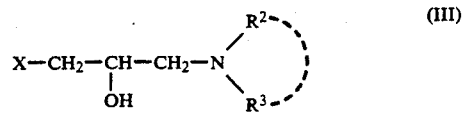

or with 3-hydroxyazetidine salts of the formula (V)

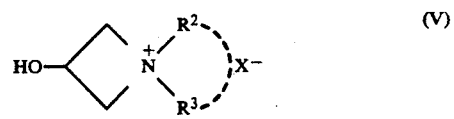

respectively. Protic solvents such as water, methanol, ethanol or mixtures of water with a water-immersible solvent, e.g. benzene were used as solvents in these reactions. The final products were isolated by extraction (sometimes after evaporation), the extract was washed several times with a concentrated alkaline solution and after solvent change it was acidified by alcoholic hydrochloric acid and carefully crystallized. The hydrochlorides of the products were obtained in yields between 6% and 50% in this way.

On reproduction and scale increase of these reactions it has surprisingly been found that the amidoximes of the formula (II)

could not completely be transformed. After a reaction of about 60 to 70%, the reaction stopped and both an increase in the reaction temperature or use of an excess of reactant enhanced the amount of tarry side products which inhibited the isolation of the product.

DESCRIPTION OF THE INVENTION

Thus, the aim of the present invention is to provide an industrial plant process which is free from the above disadvantages.

It is known from the literature (J. Am. Chem. Soc. 80, 1257 (1958); Appl. Polym. Sci. 11, 145-8 (1967); and J. Chem. Soc. 1950, 2257-2272) that amines of the formula (III) are unstable: on standing they are reversibly transformed to a cyclic salt of the formula (V) or dimerize to a dioxane derivative of the formula (VI)

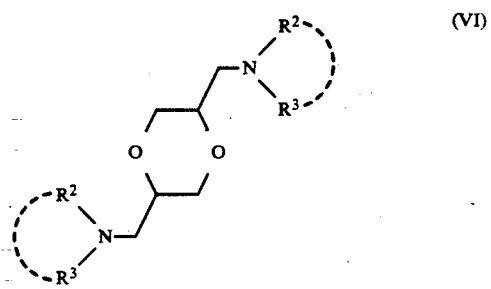

Concerning the synthesis, the former transformation is not a drawback since amidoximes can be reacted with salts of the formula (V) in the presence of a base. However, the latter transformation is irreversible which can cause a significant substance loss in the synthesis.

One basis of the present invention is the recognition that the compounds of the formulae (III), (IV) or (V), respectively, react also with water, alcohols and acids to give side products of the formula (IX)

wherein $R^4$ and $R^5$ stand for hydroxyl, $C_{1-4}$ alkoxy, $C_{2-8}$ alkanoyl or acid residue.

Depending upon the dimensions of the $R^4$ and $R^5$ groups, particularly in the case of a hydroxyl or lower alkoxy group, a polymerization of significant extent can also occur which can lead e.g. to compounds of the formula (XI)

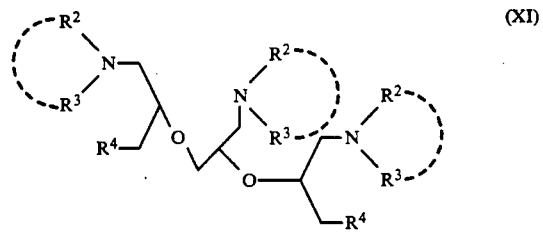

The present invention is based also on the recognition that the appearance of these decomposition products is responsible for "stopping" of the coupling reaction. The appearance of the decomposition products is presumably favorable for SN1 reactions and therefore results in a protic system promoting a further decomposition and inhibiting the reaction of amidoxime. It has been found by using model reactions that the reactants of the formulae (III), (IV) and (V) are very unstable under the conditions described up to the present and the side reactions are promoted either by basic or acidic catalysis. Thus, in the case of the epoxide of formula (IV) the basic catalysis favors a terminal substitution whereas an acid catalyst promotes the substitution on the C-2 carbon atom. In the coupling reaction with the amidoxime, the epoxide of the formula (IV) is completely decomposed within 2 to 4 hours.

Based on the above recognitions we have endeavored to find a reaction medium or reaction conditions, respectively, wherein the reactants are not decomposed and the selective coupling of the amidoxime of formula (II) and formation of the final product are promoted and accelerated either by suppressing the formation of contaminants recognized by us or by separating the final product from these contaminants which may be formed in little amounts.

Thus, the present invention relates to a process for the preparation of amidoximes of the formula (I) by reacting an amidoxime of the formula (II)

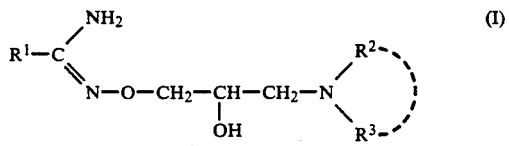

with an amine of the formula (III) and/or (IV) in the presence of a basic substance, which comprises reacting the amidoxime with an alkali metal hydroxide or alkaline metal alkoxide and dimethylformamide or 1,3-dimethyl-2-imidazolidinone, preferably in the presence of a proton source, reacting the amidoxime complex thus obtained preferably without isolation with an amine of the formulae (III) and/or (IV) and/or (V) under SN2 reaction conditions at a temperature between 0° C. and 100° C., suitably in the presence of a metal salt catalyst then, if desired, selectively separating the thus formed product of formula (I) from the side products and/or converting it with acids to salts, if desired, to mixed salts and crystallizing it or, if desired, converting it to base and/or again transforming it to a salt by using another acid.

According to a preferred embodiment of the process of the invention, the reactants of the formulae (III), (IV) and (V) are used in an excess of 0.05 to 0.15 equivalent and optionally a catalyst is employed.

It is suitable to use dimethylformamide (DMF) or N,N-dimethyl-2-imidazolidinone (DMI) with a water content of 1% or less which are free from contaminants arising e.g. from a decomposition since otherwise the yield may be deteriorated or an undesired transformation of DMF or DMI may be induced.

The formation and desired preparation, respectively, of the complex are substantial factors of the present invention. A very significant amount of precipitate was observed in a reaction carried out in dimethylformamide at 50° C. by using an alkali hydroxide as base. This precipitate gradually disappeared as the reaction proceeded. For the preparation of the complex, it is not necessary to separate it from the mixture. For improving the solubility conditions and ensuring the proton transfer it is preferred to add a proton source, preferably tertiary butanol to the mixture whereby the yield is increased by 3 to 5% and the reaction time is shortened. The complex is reacted further preferably at 30° to 75° C.

It has been stated that the purity of the starting amines of formulae (III), (IV) or (V), respectively, is important for the course of the reaction. All three compounds can excellently be reacted in a pure state whereas the purification and storage of these reactants can be solved only with difficulties on an industrial scale even because of their high reactivity. Therefore a simple method of preparing these products was developed in order to achieve an easy connection with the solution of the present invention.

It has been found that it is suitable to react the amidoxime complex prepared according to the present invention with an amine of the formulae (III), (IV) or (V), respectively, which has been prepared by reacting epichlorohydrin with an amine of the formula (VII)

in the presence of tertiary butanol taken in a ratio of 1:0.8 to 1:1.2 calculated for the mass of the amine.

Preferably, the amines of the formulae (III), (IV) or (V) are reacted with the complex without isolation from the reaction mixture after their preparation by using dimethylformamide as further solvent. In this way, the amidoxime derivative of the formula (I) can be prepared in a good yield in the same equipment (in a "one-pot" reaction).

However, the reaction lasts for a longer time owing to the inhibiting effect of the decomposition products discussed above. In these cases the use of the catalysts mentioned above is particularly preferred.

Thus, according to the present invention the preparation of the target compounds with a good efficacy has been solved simultaneously with the possible suppression of side reactions. However, as the product is accompanied by some amount of contaminating substances, the invention further relates to a selective separation of the final product from the accompanying undesired substances.

For the selective separation of the product the reaction mixture is optionally diluted with a solvent, neutralized by acid at 40° to 70° C. optionally after filtration then, optionally after a repeated filtration, the mixture is acidified, the salts and contaminations (optionally the catalyst) precipitated at a pH value of 4 to 5 at 50° C. or at a pH value of 2 to 3 at 70° C. are separated from the reaction mixture and subsequently, the salt formed from the amidoxime derivative of formula (I) with an acid is crystallized by adjusting the pH of the reaction mixture to 1 to 3. Hydrochloric acid is preferably used for the acidification.

The process according to the invention is more simple than those known up to the present and the purity of the substances obtained as crude products is essentially higher. From the point of view of the operations, it is easy to increase to an industrial scale and to realize. The yields are excellent (75 to 97%) and can further be improved by working up the mother liquors of crystallization. After evaporation and alkaline extraction of the mother liquor the solution can again be crystallized by acidification as described above.

By using the process according to the present invention it became successful to isolate in a pure crystalline state O-(2-hydroxy-3-piperidino-1-propyl) nicotinic acid amidoxime base, m.p.: 70°-73° C. which has not been described up to the present. The most important physico-chemical characteristics of this substance are as follows.

IR spectrum (KBr): $\nu$—O—C=N 1642 cm$^{-1}$
$^1$H-NMR spectrum (CDCl$_3$, $\delta$ppm): 1.48 m, (6H), CH$_2$-piperidine; 2.42 m, (6H), 3×CH$_2$N; 3.36, br, (1H), CH—O; 4.08 m, (3H), 1-CH$_2$, OH; 5.2, br, (2H), NH$_2$; 7.30 m (1H), pyridine-5'; 7.92 m, 4', 8.62 m (1H), 6', 8,88 m, (1H), 2'.

1 g of this substance dissolved in 10 ml of concentrated sulfuric acid gives a yellowish homogeneous solution.

The invention relates to this novel substance, too.

Similarly, it has been successful to obtain in a very pure state O-(2-hydroxy-3-piperidino-1-propyl) nicotinic acid amidoxime hydrochloride and hydrobromide salts. The hydrobromide has not been described at all up to the present; the hydrochloride has been published only in an unsuitable purity. The spectroscopic characteristics of these new substances are as follows.

UV spectrum: $\lambda_{max}$ 274.237 nm
IR spectrum (KBr): $\nu$—O—C=N 1649 cm$^{-1}$ $^1$H-NMR spectrum (DMSO-d$_6$, $\delta$ppm): 1.80, br, (6H), CH$_2$-piperidine; 2.65-3.75 m, (6H 3×CH$_2$—N); 4.00 m, (2H), 1-CH$_2$; 4.40 m (1H), CH—O; 7.00, br, (4H), 2×NH$^+$, NH$_2$; 8.00 dd, (1H), pyridine-5'; 8.75 m, (1H), 4'; 8.95 m, (1H), 6'; 9.13 d, (1H), 2'; 10.35, br, (1H), OH.

1 g dissolved in 10 ml of concentrated sulfuric acid gives a yellowish homogeneous solution.

SPECIFIC EXAMPLES

The process of the invention is illustrated in detail by the following non limiting Examples.

EXAMPLE 1

1.0 g (25 mmol) of powdered sodium hydroxide and 4.7 ml (50 mmol) of tert-butanol are added to the solution of 6.9 g (50 mmol) of nicotinic acid amidoxime in 50 ml of pure dry DMF. To the resulting suspension 7.8 g (55 mmol) of redistilled N-(2,3-epoxypropyl)piperidine (J. Am. Chem. Soc. 80 1257-9 (1958) are added at 50° C. and stirred at 70° C. The course of the reaction is observed by thin layer chromatography (TLC). After complete termination of the reaction the pH of the solution is adjusted to 6 and after clarifying and filtering it the filtrate is acidified to pH 2.5 and crystallized. The pale yellow crystalline precipitate is filtered to give O(2-hydroxy-3-piperidino-1-propyl) nicotinic acid amidoxime dihydrochloride in 16.5 g (94%) yield, m.p.: 202°-204° C. after recrystallization from ethanol. The first generation is 14.9 g of pale yellow product which is 99.1% purity based on displacement method or on the determination of Cl$^-$ and 99.2% based on spectrophotometric and nitrogen determination, m.p.: 202°-204° C. The yield is 85%.

UV spectrum: $\lambda_{max}$ 274.237 nm
IR spectrum (KBr): $\lambda$ —O—C=N 1649 cm$^{-1}$
$^1$H-NMR spectrum (DMSO-d$_6$, $\delta$ ppm): 1.80, br, (6H), CH$_2$-piperidine; 2.65-375 m, (6H, 3×CH$_2$—N); 4.00 m, (2H), 1-CH$_2$; 4.40 m, (1H), CH—O; 7.00, br, (4H) 2×NH$^+$, NH$_2$; 8.00 dd, (1H), pyridine-5'; 8.75 m, (1H), 4'; 8.95 m, (1H), 6'; 9.13 d, (1H), 2'; 10.35, br. (1H), OH.

1 g of the product dissolved in 10 ml of concentrated sulfuric acid gives a yellowish homogeneous solution.

EXAMPLE 2

435 ml of dry tert-butanol and 676 g (4.785 mol) of N-(2,3-epoxypropyl)piperidine are added to the mixture containing 596 g (4.35 mol) of nicotinic acid amidoxime, 4350 ml of pure dry DMF and 100 g (2.5 mol) of sodium hydroxide. The pale brown suspension is stirred at 65° C. for 3 hours. The course of the reaction is observed as described in Example 1. After acidifying the mixture to pH=6 it is clarified, filtered and the dark yellow solution is adjusted to pH 2.5. The pale yellow crystalline precipitate is filtered to give 1480 g of O(2-hydroxy-3-piperidino-1-propyl) nicotinic acid amidoxime dihydrochloride in a purity of 95%. The yield is 92%. After recrystallization the total yield together with the second and third generations amounts to 88% calculated for the starting substances. The purity of the crystallized product is 99.5%, m.p.; 202°-204° C. The product is identical to that of Example 1.

EXAMPLE 3

After mixing 41.3 g of nicotinic acid amidoxime, 750 ml of dry DMF and 6 g of NaOH, 46.6 g of N-(2,3-epoxypropyl)piperidine were added to the complex obtained and the mixture is reacted at 65° C. for 4 hours. Meantime the orange red thick suspension is transformed to a pale brown solution corresponding to the course of the reaction. After distilling off 400 ml of DMF from the solution over 90 minutes the mixture is cooled to room temperature and diluted with 500 ml of dry isopropanol.

After adjusting the pH of the solution to 6 to 7 and then filtering off the contaminations, the pH of the pale yellow solution is adjusted to 2.5 by adding hydrochloric acid and left to slowly crystallize. 81 g of butter-colored crystalline hydrochloride are obtained, m.p.: 202°–205° C. This product is analytically identical to those described in the preceeding Examples. From the mother liquor 14.5 g of pale yellow crystalline product are obtained as 2nd generation, m.p.: 195°–200° C. The total yield amounts to 90.6%.

EXAMPLE 4

By treating O(2-hydroxy-3-piperidino-1-propyl)nicotinic acid amidoxime dihydrochloride with sodium hydroxide solution the base is obtained and as a white crystalline substance O-(2-hydroxy-3-piperidino-1-propyl) nicotinic acid amidoxime is isolated in a pure state, m.p.: 70°–73° C.

IR spectrum (KBr): $\nu$ —O—C=N— 1642 cm$^{-1}$ $^1$H-NMR spectrum (CDCl$_3$, $\delta$ ppm): 1.48 m, (6H), CH$_2$-piperidine; 2.42 m, (6H), 3×CH$_2$N; 3.35, br, (1H), CH—O; 4.08 m, (3H), 1-CH$_2$, OH; 5.2 br, (2H), NH$_2$; 7.30 m, (1H), pyridine 5'; 7.92 m, (1H), 4'; 8.62 m, (1H), 6'; 8.88 m, (1H), 2'.

1 g of this substance dissolved in 10 ml of concentrated, sulfuric acid gives a yellowish homogeneous solution.

EXAMPLE 5

O-(2-hydroxy-3-piperidino-1-propyl) nicotinic acid amidoxime is prepared as described in Example 1, except that the acidification is carried out by an ethanolic solution of dry hydrogen bromide to obtain 20.5 g of O(2-hydroxy-3-piperidino-1-propyl) nicotinic acid amidoxime dihydrobromide in a yield of 93% (together with the 2nd generation), m.p.: 180°–184° C.

EXAMPLE 6

The process described in Example 1 is followed, except that the salt is formed by using an isopropanolic solution saturated by dry hydrogen chloride (with a concentration of about 8.5 mmol/ml) to give O(2-hydroxy-3-piperidino-1-propyl) nicotinic acid amidoxime dihydrochloride in a yield of 95%.

EXAMPLE 7

The process described in Example 1 is followed, except that no tert-butanol is used. The reaction mixture is stirred for 6 hours at 70° C. to give a total yield of 94%.

EXAMPLE 8

The process described in Example 1 is followed, except that no tert-butanol is used and 1.12 g (10 mmol) of potassium tert-butoxide are employed as base. After stirring the reaction mixture at 70° C. for 3 hours a total yield of 16.67 g (95%) is obtained.

EXAMPLE 9

The process described in Example 1 is followed, except that 70 ml of DMF, 5.0 g (125 mmol) of sodium hydroxide are used as reactant 11.8 g (55 mol) of 1-chloro-2-hydroxy-3-piperidinopropane hydrochloride (Monatshefte für Chemie, 15, 119) are added. After stirring the reaction mixture at 70° C. for 6 hours the product is obtained in a total yield of 16.7 g (95%).

EXAMPLE 10

The process described in Example 1 is followed, except that 3.2 g (80 mmol) of powdered sodium hydroxide, 7.5 ml of tert-butanol are used and as reactant 9.8 g (55 mmol) of 1,1-pentamethylene-3-hydroxyazetidinium chloride (J. Org. Chem. 33 (2) 523) are added. After stirring the suspension at 70° C. for 3 hours O(2-hydroxy-3-piperidino-1-propyl) nicotinic acid amidoxime dihydrochloride is obtained in a total yield of 15.8 g (90%).

EXAMPLE 11

The process described in Example 1 is followed, except that 1.0 g (10 mmol) of aluminum oxide is used as catalyst. After recrystallization the product is obtained in a yield of 14.9 g (85%), m.p.: 206°–209° C.

EXAMPLE 12

The process described in Example 1 is followed, except that 1.5 g (10 mmol) of stannic oxide are used as catalyst. After recrystallization the product is obtained in a yield of 14.7 g (84%), m.p.: 207°–210° C.

EXAMPLE 14

The process described in Example 1 followed, except that 9.3 g (50 mmol) of 2-amino-5-chlorobenzamidoxime are used as acid amidoxime component and after acidification the reaction mixture is evaporated under reduced pressure. The thick oily residue is dissolved in 50 ml of hot isopropanol and left to crystallize to give a yield of 15.0 g, m.p.: 189°–190° C.

EXAMPLE 15

4.7 g (5.5 ml; 55 mmol) of piperidine are added over 20 minutes to the solution of 5.1 g (4.3 ml; 55 mmol) of epichlorohydrin in 5.2 ml of tert-butanol under cooling by water while stirring vigorously. The reaction mixture is stirred at room temperature for 1 hour, then 50 ml of pure dry DMF, 6.9 g (50 mmol) of nicotinic acid amidoxime and 3.2 g (80 mmol) of powdered sodium hydroxide are added. After stirring the suspension at 70° C. for 12 hours the reaction mixture is worked up as described in Example 1 to give 13.2 g (75%) of O(3-amino-2-hydroxypropyl) nicotinic acid amidoxime dihydrochloride.

EXAMPLES 16 TO 26

General process for the preparation of O-alkylated acid amidoxime derivatives of the formula (I).

Method A 50 mmol of an acid amidoxime of the formula (II) are dissolved in 50 ml of pure dry DMF, then 25 mmol of a basic catalyst, 4.7 ml (50 mmol) of tert-butanol and finally 55 mmol of an 1-(2,3-epoxypropyl)amine of the formula (IV) are added.

After stirring at 70° C. until complete termination of the reaction, the mixture is acidified as described in Example 1 and then the product of the formula (I) is isolated.

Method B

The process described under method A is followed, except that the reaction mixture is acidified and evaporated as described in Example 14 and the product obtained is crystallized from a solvent.

Method C

The process described under method A is followed, except that the free base is liberated as described in Example 4 and then is crystallized from a solvent or isolated as an oil.

We claim:

1. A pure O-(2-hydroxy-3-piperidino-1-propyl) nicotinic acid amidoxime hydrochloride of the Formula (Ia)

| Example No. | R¹ | N(R¹)(R²) | Time of reaction hour | Catalyst | Method | Isolated form | Crystallization solvent | m.p. °C. |
|---|---|---|---|---|---|---|---|---|
| 16 |  | 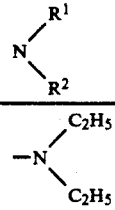 | 4 | NaOH | B | HCl salt | Ethanol/izopropanol | 78–81 |
| 17 |  | 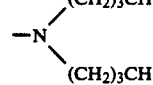 | 13 | NaOH | B | HCl salt | Acetonitrile | 77–80 |
| 18 |  | 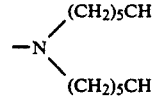 | 15 | NaOH | B | HCl salt | Acetonitrile | 110–116 |
| 19 |  | 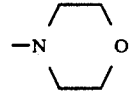 | 8 | NaOH | B | HCl salt | abs. Ethanol | 92–99 |
| 20 |  | 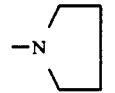 | 15 | NaOH | | | abs. Ethanol | 175–177,5 |
| 21 |  | 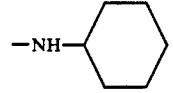 | 22 | NaOH | C | Base | Diethyl ether | 90–93 |
| 22 |  | 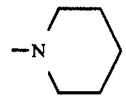 | 23 | NaOH | A | HCl salt | DMF | 219–221 |
| 23 |  | 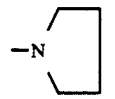 | 18 | NaOH | B | HCl salt | Izopropanol | 204–212 |
| 24 |  | 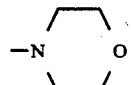 | 8 | NaOH | B | HCl salt | Acetonitrile | 157–162 |
| 25 | 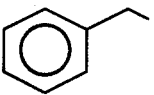 | 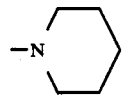 | 32 | KOtBu | C | Base | Petrolether | 94–97 |
| 26 | 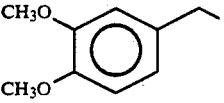 | 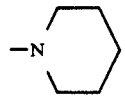 | 23 | KOtBu | B | HCl salt | DMF | 202–203 |

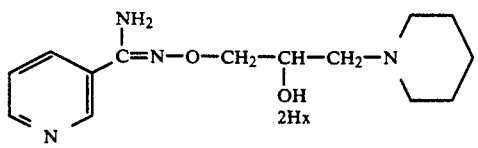

wherein X is chloride;
characterized by giving, when dissolved in an amount of 1 to 10 ml of concentrated sulfuric acid, a yellow homogeneous solution, and showing the following spectral characteristics:

UV spectrum: $\lambda_{max}$ 274.237 nm
IR spectrum: (kBr): $\nu$ —O—C=N 1649 cm$^{-1}$
$^1$H-NMR spectrum (DMSO-d$_6$, δ ppm): 1.80, br, (6H), CH$_2$-piperidine; 2.65-3.75 m, (6H$_1$ 3×CH$_2$—N); 4.00 m, (2H), 1-CH$_2$; 4.40 m (1H), CH—O; 7.00, br, (4H), 2×NH$^+$, NH$_2$; 8.00 dd, (1H), pyridine-5'; 8.75 m, (1H), 4'; 8.95 m, (1H), 6'; 9.13 d, (1H), 2'; 10.35, br, (1H), OH.

* * * * *